United States Patent [19]

Gayso

[11] Patent Number: 5,007,836
[45] Date of Patent: Apr. 16, 1991

[54] GROOVE LOCK DENTAL BRIDGE ATTACHMENT AND METHOD

[76] Inventor: Donald W. Gayso, 1092 Perkins Ter., Memphis, Tenn. 38115

[21] Appl. No.: 198,875

[22] Filed: May 26, 1988

[51] Int. Cl.⁵ .................................. A61C 13/12
[52] U.S. Cl. ............................. 433/181; 433/76; 433/182; 433/213; 433/223
[58] Field of Search ............... 433/180, 181, 182, 183, 433/141, 213, 223, 76

[56] References Cited

U.S. PATENT DOCUMENTS

| | | | |
|---|---|---|---|
| 1,394,299 | 10/1921 | Foster | 433/180 |
| 1,478,019 | 12/1923 | Brown | 433/213 |
| 1,753,644 | 4/1930 | Burden | 433/181 |
| 2,448,437 | 8/1948 | Kaplan | 433/76 |
| 2,634,501 | 4/1953 | Linet | 433/76 |
| 3,442,015 | 5/1969 | Goodman | 433/181 |
| 4,260,383 | 4/1981 | Weissman | 433/76 |
| 4,474,499 | 10/1984 | Pedrazzini | 433/181 |
| 4,571,186 | 2/1986 | Pipko | 433/213 |
| 4,627,136 | 12/1986 | Kreylos et al. | 433/223 |

Primary Examiner—John J. Wilson
Attorney, Agent, or Firm—Walker & McKenzie

[57] ABSTRACT

An artificial dental appliance for bridging the distance between two adjacent teeth. The appliance includes a bridge for filling the space between the two adjacent teeth and retaining structure for securing the bridge to the two adjacent teeth. The retaining structure includes a pin for extending transversely through a groove formed in the side of one of the teeth and through a groove formed in one side of the bridge.

14 Claims, 2 Drawing Sheets

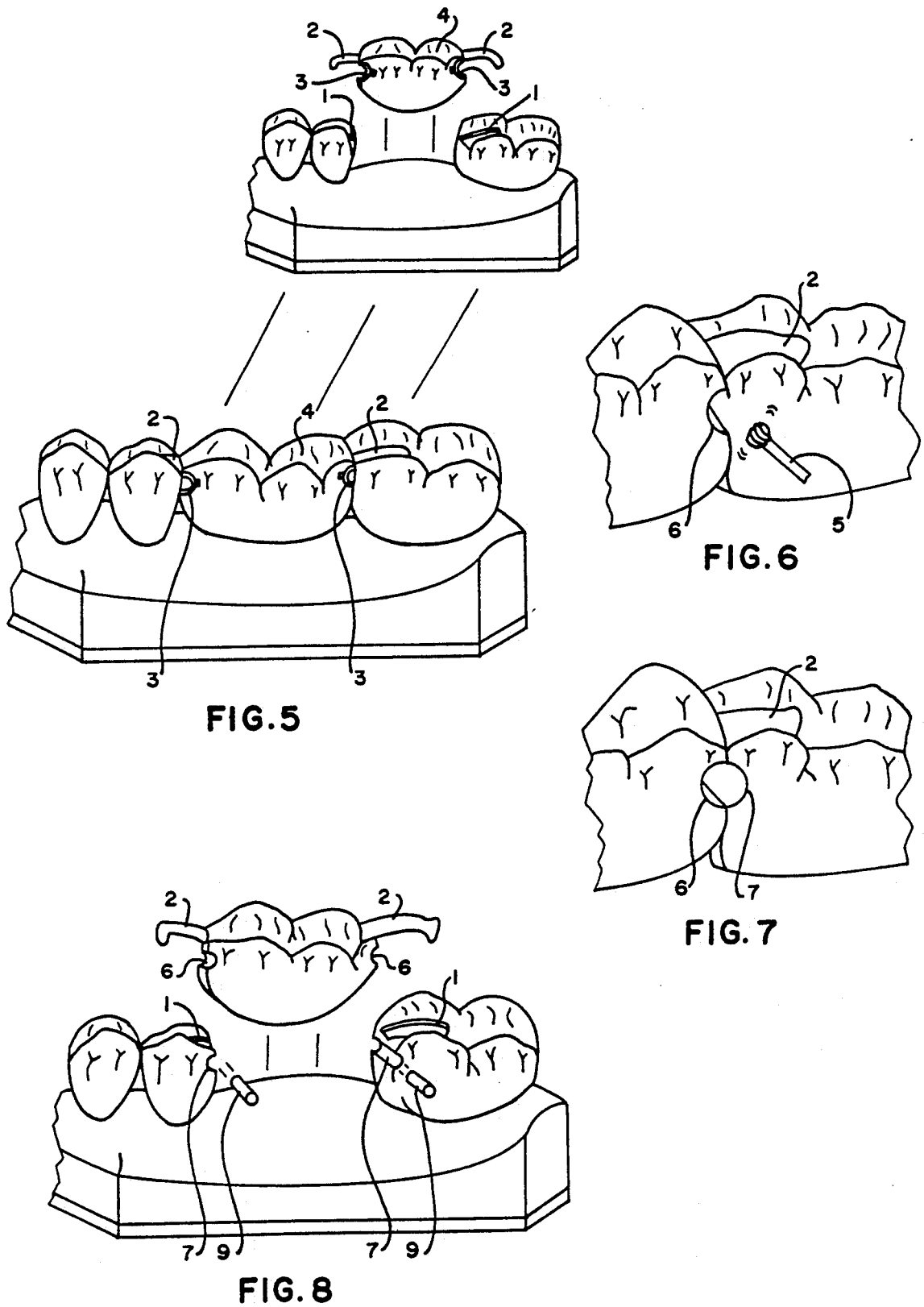

GROOVE LOCK DENTAL BRIDGE ATTACHMENT AND METHOD

FIELD OF THE INVENTION

The present invention relates to the field of dentistry. It is the apparatus and process for the construction and anchoring of a dental appliance.

BACKGROUND

Numerous proposals have been advanced over the years for the replacement of missing teeth. Many of these proposals were designed to meet a specific set of circumstances involved in different patients. This invention is a groove lock anchoring means for attaching an artificial tooth to existing teeth. Although the groove lock anchoring means can utilized for a variety of circumstances in the mouth that require an anchoring means, it relates primarily to the circumstances where the patient requires the replacement and anchorage of a single tooth which is between two good adjacent teeth. The two good teeth are called abutment teeth when they are used to support or retain an artificial appliance.

One prior attempt at anchoring a single tooth in place meant the use of wire like members called clasps. These clasps held the replacement tooth in position with a clamping action around the surrounding teeth. This type of appliance which utilizes clasps as an anchoring means, is many times bulky and uncomfortable. They are also removable. They are commonly called removable partial bridges. Somewhat similar in design to the removable partial bridges is a bridge developed at the University of Maryland. This bridge is called the Maryland Bridge. The Maryland Bridge is not removable. The clasps, or wings as they are commonly called with the Maryland Bridge, are not retained with a clamping action. They are permanently retained with cementations. The wings of the Maryland Bridge can catch and retain food. This makes the Maryland Bridge harder to clean and could invite an unsanitary condition for the patient.

Another prior attempt at replacing a missing tooth that is situated between two good adjacent teeth is called a three unit bridge. To position a three unit bridge, the dentist must grind down to prepare the two good adjacent teeth so that they can accept crowns, or caps as they are sometimes called. To span the space of the missing tooth, an artificial tooth is constructed and connected with crowns that fit on the prepared adjacent teeth. These adjacent teeth are functioning as abutment teeth. The three unit bridge is a good dental appliance, as is the removable partial bridge and the Maryland Bridge, but it requires additional preparation of the adjacent teeth and the extra work and expense involved with the utilization of the two extra crowns on the adjacent teeth.

My invention is fast, effective, and overcomes many to the objections commensurate with the prior attempts. It is permanent and more comfortable than a removable partial bridge. It does not have wings to catch and retain food as does the Maryland Bridge. It requires less preparation and is more cost effective than a three unit bridge.

BRIEF DESCRIPTION OF DRAWINGS

FIG. 5 is a perspective view of the wax pattern containing the pre-formed pattern. This view shows the wax pattern before and after it is removed from the working cast.

FIG. 6 is a perspective view depecting how the primary retainer groove in the bridge serves to guide the drilling bur to form the secondary retainer grooves in the adjacent tooth.

FIG. 7 is a perspective view showing the completed drilling of the secondary retainer grooves.

FIG. 8 is an exploded perspective view denoting the locking action of the groove lock bridge attachment.

DESCRIPTION OF PROCESS AND EMBODIMENT

To prepare the patients adjacent teeth to accept a groove lock bridge and attachment, the dentist must first design and grind in the locking rest areas 1 that are shown in FIGS. 1,2, 4,5, and 8. These locking rest areas are cutout areas in the abutment teeth into which extensions 2 from the groove lock bridge will later rest. The extensions 2 are shown in FIGS. 5,6,7, and 8.

After completing the preparation of the locking rest areas in the patients' teeth, the dentist takes an impression of the patients' teeth from which a working model or cast is made. The working cast is made by the conventional method of pouring a plaster like material into the said impression of the patients' teeth. After the plaster like material hardens, it is removed from the impression and is a duplication of the patients' teeth. The working cast is seen in our accompanying drawings. It will be the model on which the groove lock bridge is constructed.

Figure 1:
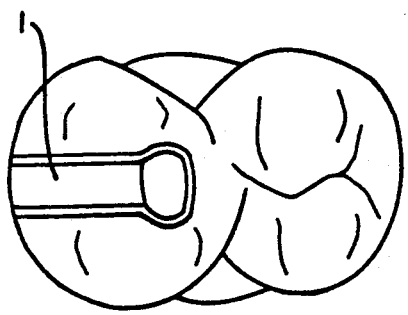
FIG. 1 is a top occlusial or chewing surface view of an adjacent tooth showing preferred preparation of the locking rest area.
Figure 2:
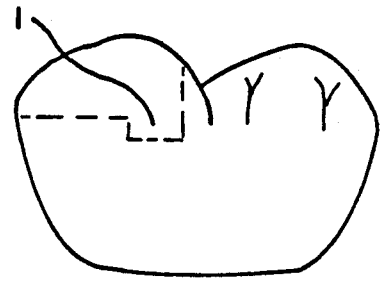
FIG. 2 is a side view of a adjacent tooth showing preferred preparation of a locking rest area.
Figure 3:
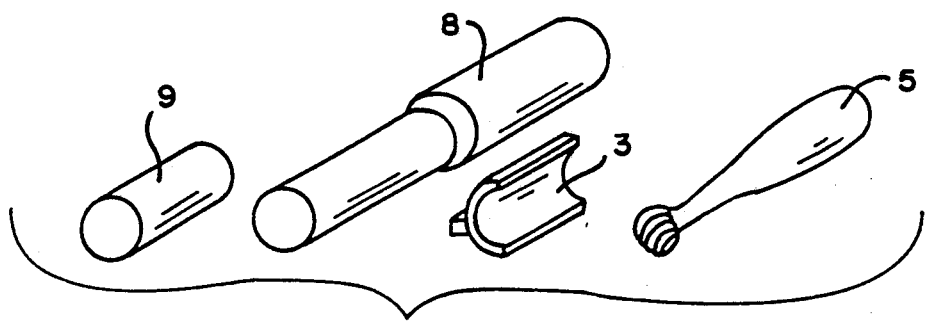
FIG. 3 is a perspective view of the apparatus required for the construction and anchorage of the groove lock dental bridge attachment.
Figure 4:
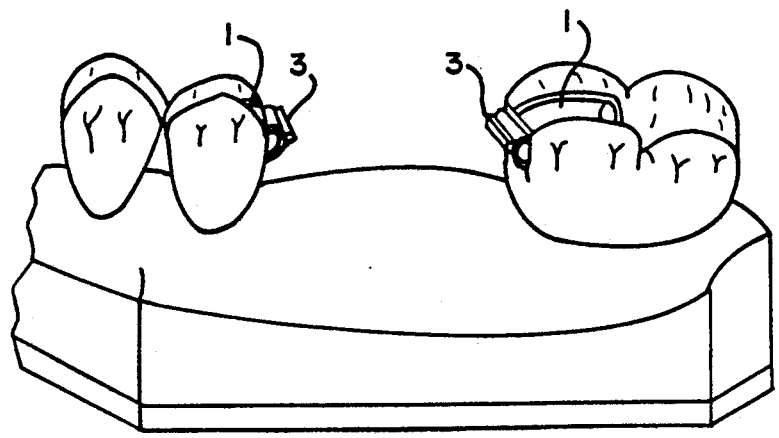
FIG. 4 is a perspective view showing the pre-formed patterns positioned on the working cast.

To construct the groove lock bridge the pre-formed patterns 3, FIGS. 3 and 4, are positioned on the working cast and lightly held in place with a suitable material as shown in FIG. 4. It should be noted that the longitudinal profile of the pre-formed pattern is a portion of a circle. Its portion of a complete circle is approximately on half.

Utilizing a process called a wax-up, a wax model of the desired form of the groove lock bridge is carved. The said pre-formed patterns are contained within the wax model 4, in FIG. 5. Since the pre-formed patterns were held lightly in place on the working cast with a suitable material, the wax model 4, containing the said pre-formed patterns 3, can be easily removed from the working cast as shown in FIG. 5. The function of the pre-formed patterns 3 is to give the exact desired size and form to the grooved areas of the wax model 4. The pre-formed patterns 3, like the rest of the wax model 4, must be capable of burning out of a casting mold using a conventional casting technique called lost wax casting.

Lost wax casting is a casting technique in which a material capable of withstanding a high temperature is poured around the wax model and allowed to harden. The material containing the wax model is then heated until the wax model burns out leaving a void that is an exact negative reproduction of the wax model. Molten metal is then introduced into the void and gives an exact reproduction of the wax model in metal.

Using the conventional technique called lost wax casting an exacting reproduction of the wax model 4 is made out of an acceptable dental alloy or material. This acceptable dental alloy or material should be harder than the patients own tooth structure. The reason for this said hardness will become apparent later.

The dentist can now seat and anchor the groove lock bridge onto the patients teeth. To do this, the dentist first seats and holds the groove lock bridge in its proper position on the patients' teeth.

Using the drilling bur 5, whose diameter coincides with that of the longitudinal profile of the groove 6, in the groove lock bridge, the dentist grinds or drills an associated groove 7 into the patients adjacent teeth. During this drilling process, the grooves 6 in the groove lock bridge functions as drilling guides for drilling the associated grooves 7 in the patients adjacent abutment teeth. The dentist can drill the said associated groove 7 in the patients adjacent teeth with no appreciable distortion to the grooves 6 in the groove lock bridge because the grooves 6 in the said groove lock bridge were formed in an alloy or material harder than the patients' own tooth structure. The drilling process is depicted in FIGS. 6 and 7.

To check the function of the groove lock bridge in the patients mouth, temporary retainer pins 8 of FIG. 3 are inserted to temporarily hold the groove lock bridge in place. These temporary retainer pins 8 make it easy for the dentist to insert and remove the groove lock bridge if any adjustments are necessary. For permanent placement in the patients mouth, the groove lock bridge and permanent retainer pins 9 of FIGS. 3 and 8 are cemented in place. The permanent retainer pins 9 can be threaded or contain small grooving for added retention with the cement. Although the stainless steel permanent retainer pins 9 work well for this invention, some of todays dental materials that will adhere to the bridge material and tooth structure may work with this process technique equally as well when they are injected into the grooves 6 and 7 and allowed to harden. The exploded perspective view FIG. 8 denotes the locking action of the groove lock bridge.

It is realized that various embodiments may work for this invention equally as well and it is my intention that the following claims be given a scope commensurate with the broadest interpretation of the employed language.

I claim:

1. An artificial dental appliance for being positioned between adjacent first and second abutment teeth, each of said abutment teeth having an outer end and being modified to have a groove in said outer end thereof, said appliance comprising:
   (a) bridge means for extending between said outer end of said first abutment tooth and said outer end of said second abutment tooth, said bridge means having a first side for being positioned adjacent said outer end of said first abutment tooth and having a second side for being positioned adjacent said outer end of said second abutment tooth, said first side of said bridge means having a groove therein, said second side of said bridge means having a groove therein; said groove in said outer end of said first abutment tooth and said groove in said first side of said bridge means being aligned with one another when said appliance is positioned between said abutment teeth; said groove in said outer end of said second abutment tooth and said groove in said second side of said bridge means being aligned with one another when said appliance is positioned between said abutment teeth;
   (b) first securing means for securing said first side of said bridge means to said first abutment tooth, said first securing means including retaining means for being inserted into said groove in said outer end of said first abutment tooth and said groove in said first side of said bridge means; said retaining means of said first securing means including a retaining pin for being inserted into said groove in said outer end of said first abutment tooth and said groove in said first side of said bridge means; and
   (c) second securing means for securing said second side of said bridge means to said second abutment tooth, said second securing means including retaining means for being inserted into said groove in said outer end of said second abutment tooth and said groove in said second side of said bridge means; said retaining means of said second securing means including a retaining pin for being inserted into said groove in said outer end of said second abutment tooth and said groove in said first side of said bridge means; each of said retaining pins including a handle portion for allowing easy removal thereof.

2. An artificial dental appliance for being positioned between adjacent first and second abutment teeth, each of said abutment teeth having an outer end and being modified to have a groove in said outer end thereof, said appliance comprising:
   (a) bridge means for extending between said outer end of said first abutment tooth and said outer end of said second abutment tooth, said bridge means having a first side for being positioned adjacent said outer end of said first abutment tooth and having a second side for being positioned adjacent said outer end of said second abutment tooth, said first side of said bridge means having a groove therein, said second side of said bridge means having a groove therein; said groove in said outer end of said first abutment tooth and said groove in said first side of said bridge means being aligned with one another when said appliance is positioned between said abutment teeth; said groove in said outer end of said second abutment tooth and said groove in said second side of said bridge means being aligned with one another when said appliance is positioned between said abutment teeth;
   (b) first securing means for securing said first side of said bridge means to said first abutment tooth, said first securing means including retaining means for being inserted into said groove in said outer end of said first abutment tooth and said groove in said first side of said bridge means; said retaining means of said first securing means including a retaining pin for being inserted into said groove in said outer end of said first abutment tooth and said groove in said first side of said bridge means; and
   (c) second securing means for securing said second side of said bridge means to said second abutment tooth, said second securing means including retaining means for being inserted into said groove in said outer end of said second abutment tooth and said groove in said second side of said bridge means; said retaining means of said second securing means including a retaining pin for being inserted into said groove in said outer end of said second abutment tooth and said groove in said first side of said bridge means;

(d) a first extension member having a first end fixedly attached to said bridge means and having a second end for being attached to said first abutment tooth.

3. The appliance of claim 2 in which is included a second extension member having a first end fixedly attached to said bridge means and having a second end for being attached to said second abutment tooth.

4. The appliance of claim 3 in which said first abutment tooth is modified to have a cutout area; and in which said second end of said first extension member includes a head portion for extending into said cutout area of said first abutment tooth.

5. The appliance of claim 4 in which said second abutment tooth is modified to have a cutout area; and in which said second end of said second extension member includes a head portion for extending into said cutout area of said second abutment tooth.

6. The appliance of claim 5 in which each of said abutment teeth has an occlusial surface, and in which said groove in said outer end of each of said abutment teeth extends across said abutment teeth in a direction parallel to said occlusial surfaces thereof.

7. The appliance of claim 6 in which said bridge means has an occlusial surface, and in which said grooves in said first and second sides of said bridge means extend across said bridge means in a direction parallel to said occlusial surface thereof.

8. An artificial dental appliance for being positioned between adjacent first and second abutment teeth, each of said abutment teeth having an outer end and an occlusial surface, each of said abutment teeth being modified to have a groove in said outer end thereof extending thereacross in a direction parallel to said occlusial surface thereof and having a cutout area in said occlusial surface thereof; said appliance comprising:

(a) bridge means for extending between said outer end of said first abutment tooth and said outer end of said second abutment tooth, said bridge means having a first side for being positioned adjacent said outer end of said first abutment tooth and having a second side for being positioned adjacent said outer end of said second abutment tooth, said first side of said bridge means having a groove therein, and said second side of bridge means having a groove therein;

(b) first securing means for securing said first side of said bridge means to said first abutment tooth, said first securing means including retaining means for being positioned in and extending between said groove in said outer end of said first abutment tooth and said groove in said first side of said bridge means; said retaining means of said first securing means including a retaining pin for being inserted into said groove in said outer end of said first abutment tooth and said groove in said first side of said bridge means;

(c) second securing means for securing said second side of said bridge means to said second abutment tooth, said second securing means including retaining means for being positioned in and extending between said groove in said outer end of said second abutment tooth and said groove in said second side of said bridge means; said retaining means of said second securing means including a retaining pin for being inserted into said groove in said outer end of said second abutment tooth and said groove in said first side of said bridge means;

(d) a first extension member having a first end fixedly attached to said bridge means and having a second end for being attached to said first abutment tooth; said second end of said first extension member including a head portion for extending into said cutout area of said first abutment tooth; and (e) a second extension member having a first end fixedly attached to said bridge means and having a second end for being attached to said second abutment tooth; said second end of said second extension member including a head portion for extending into said cutout area of said second abutment tooth.

9. A method of constructing an artificial dental appliance and anchoring said appliance to adjacent first and second abutment teeth, each of said abutment teeth having an outer end, said method comprising the steps of:

(a) building a model bridge means between said outer end of said first abutment tooth and said outer end of said second abutment tooth;

(b) making an actual bridge means in an exact reproduction of said model bridge means out of an acceptable dental material; said actual bridge means having a first side for being positioned adjacent said outer end of said first abutment tooth and having a second side for being positioned adjacent said outer end of said second abutment tooth;

(c) forming a groove in said first side of said actual bridge means;

(d) seating said actual bridge means in position between said first and second abutment teeth;

(e) drilling a groove in said outer end of said first abutment tooth using said groove in said first side of said actual bridge means as a guide;

(f) inserting first securing means into said grooves in said first side of said actual bridge means and said outer end of said first abutment tooth for securing said first side of said actual bridge means to said first abutment tooth; and (g) securing said second side of said actual bridge means to said second abutment tooth.

10. A method of constructing an artificial dental appliance and anchoring said appliance to adjacent first and second abutment teeth, each of said abutment teeth having an outer end, said method comprising the steps of:

(a) building a model bridge means between said outer end of said first abutment tooth and said outer end of said second abutment tooth;

(b) making an actual bridge means in an exact reproduction of said model bridge means out of an acceptable dental material; said actual bridge means having a first side for being positioned adjacent said outer end of said first abutment tooth and having a second side for being positioned adjacent said outer end of said second abutment tooth;

(c) forming a groove in said first side of said actual bridge means;

(d) forming a groove in said second side of said actual bridge means;

(e) seating said actual bridge means in position between said first and second abutment teeth;
(f) drilling a groove in said outer end of said first abutment tooth using said groove in said first side of said actual bridge means as a guide;
(g) drilling a groove in said outer end of said second abutment tooth using said groove in said second side of said actual bridge means as a guide;
(h) inserting first securing means into said grooves in said first side of said actual bridge means and said outer end of said first abutment tooth for securing said first side of said actual bridge means to said first abutment tooth; and
(i) inserting second securing means into said grooves in said second side of said actual bridge means and said outer end of said second abutment tooth for securing said second side of said actual bridge means to said second abutment tooth.

11. The method of claim 10 in which the steps of forming grooves in said first and second sides of said actual bridge means includes the steps of attaching a first pattern to said outer end of said first abutment tooth and attaching a second pattern to said outer end of said second abutment tooth before said model bridge means is built between said outer end of said first abutment tooth and said outer end of said second abutment tooth.

12. The method of claim 11 in which said steps of making an actual bridge means includes the step of making a lost wax casting of said model bridge means.

13. The method of claim 12 in which said step of inserting first securing means into said grooves in said first side of said actual bridge means and said outer end of said first abutment tooth includes the step of inserting a retaining pin into said grooves in said first side of said actual bridge means and said outer end of said first abutment tooth.

14. The method of claim 13 in which said step of inserting second securing means into said grooves in said second side of said actual bridge means and said outer end of said second abutment tooth includes the step of inserting a retaining pin into said grooves in said second side of said actual bridge means and said outer end of said second abutment tooth.

* * * * *